United States Patent [19]

Bellifemine

[11] Patent Number: 5,800,504
[45] Date of Patent: Sep. 1, 1998

[54] PORTABLE DEVICE FOR TREATING INSECT BITES

[75] Inventor: Francesco Bellifemine, Varese, Italy

[73] Assignee: La Tecnica S.r.l., Italy

[21] Appl. No.: 763,712

[22] Filed: Dec. 13, 1996

[30]  Foreign Application Priority Data

Jan. 19, 1996 [IT] Italy ............................. MI96A0085

[51] Int. Cl.⁶ ..................................................... A61N 1/32
[52] U.S. Cl. ................................ 607/145; 607/72; 607/115
[58] Field of Search ............................... 607/145, 72, 115, 607/148; 361/232; 273/84

[56]  References Cited

U.S. PATENT DOCUMENTS

| | | | |
|---|---|---|---|
| 3,758,827 | 9/1973 | Schroder et al. | 317/81 |
| 3,826,952 | 7/1974 | Iwasaki et al. | |
| 3,829,737 | 8/1974 | Johnsson | 317/81 |
| 4,297,609 | 10/1981 | Hirao et al. | |
| 4,315,180 | 2/1982 | Kondo et al. | 310/319 |
| 4,741,347 | 5/1988 | Robert et al. | 607/150 |
| 4,873,609 | 10/1989 | Mackey | |
| 5,074,305 | 12/1991 | Guderian | 607/72 |
| 5,235,990 | 8/1993 | Dempsey | 607/145 |
| 5,496,356 | 3/1996 | Hudz | 607/145 |

FOREIGN PATENT DOCUMENTS

| | | | |
|---|---|---|---|
| WIPO | | | |
| 8704068 | 7/1987 | France | 607/145 |
| 1448644 | 9/1976 | United Kingdom | 607/145 |

*Primary Examiner*—John P. Lacyk
*Assistant Examiner*—David M. Ruddy
*Attorney, Agent, or Firm*—Laff, Whitesel, Conte & Saret, Ltd.

[57]  ABSTRACT

It is described a portable device for treating insect bites comprising a piezoelectric body (5a; 108) to be operated by a striker (19; 107) to generate a predetermined voltage at the ends of two electrodes or between one electrode and the user's body.

12 Claims, 3 Drawing Sheets

PORTABLE DEVICE FOR TREATING INSECT BITES

FIELD AND BACKGROUND OF THE INVENTION

The present invention relates to a portable device for treating insect bites.

Presently many products and devices are adapted for treatment of mosquito, wasp and bee bites or even more severe bites such as those made by scorpions or vipers.

In particular, many of the products are based on ammonia. These products however are scarcely able to soothe irritations caused by bites and have time limited effects.

Beside the above described products, many known devices are capable of treating the bitten area by heating up to 50°–60° C. (see French Patent 1139096).

Other known devices are capable of producing a low-voltage direct current from a small storage battery to the bitten area (see U.S. Pat. No. 4,982,743).

The above devices however have little flexibility because a rather long time is required for reaching good results in terms of bite treatment.

Due to the above limitation, it is also impossible for several persons to simultaneously use the above devices.

In any case, such devices have to be provided with a storage battery thereby increasing costs and requiring periodical recharge.

Another type of known devices comprises a structure capable of producing electric discharges of very high voltage and very low current (see U.S. Pat. No. 5,350,416; U.S. Pat. No. 4,873,609; and Italian Patent MI92U001079).

These devices also have several drawbacks.

First of all, the circuit required for increasing the electric voltage has such an intrinsic cost that the overall cost of the devices is greatly increased.

In addition, due to the intensity of the electric discharge produced, use of these devices is only justified when very serious cases are to be treated.

At all events, these devices are adapted for use on adults only because the electric discharge has such an intensity that it is rather painful by itself and therefore can be hardly used on children.

In addition, these devices require the use of storage batteries. This results in additional costs and requires periodical recharging or replacing of the storage batteries.

SUMMARY OF THE INVENTION

It is an object of the present invention to provide a new portable device for treating insect bites, capable of overcoming the above mentioned drawbacks.

In particular, it is an object of the invention to provide a device capable of continuously operating without requesting periodical recharge.

Another object of the invention is to provide a device that has an easy and ready setting so that its use may be very practical and intuitive.

A further object of the invention is to provide a device of simple structure and inexpensive to manufacture with components easily available on the market.

Another important object of the invention is to provide a device capable of producing electric discharges suitable for treatment of small-insect bites and adapted for repeated use on children without causing too much worry or pain.

These and other objects of the present invention will become apparent from the following description and drawings.

DESCRIPTION OF THE PREFERRED EMBODIMENT

Figure 1:
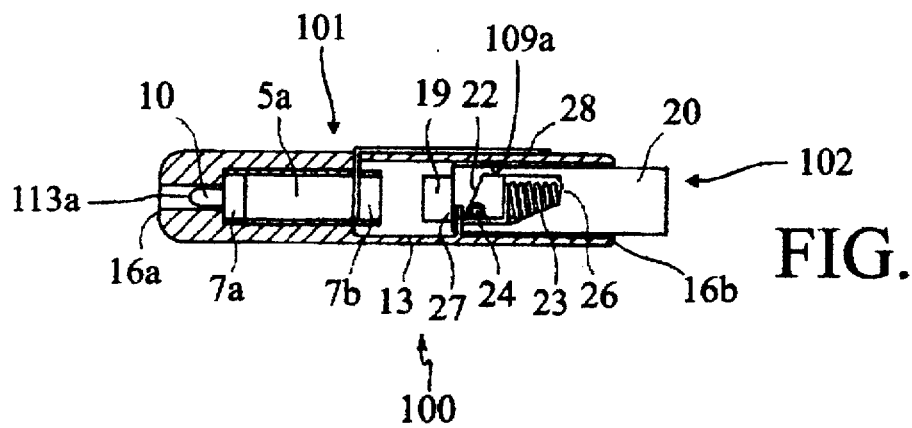
FIG. 1 is a partly sectional longitudinal view of a first embodiment of the device according to the present invention.

With reference to the drawings, a portable device for treating insect bites has been generally identified by reference numeral 100. The device comprises voltage-generator 101 defined by at least a piezoelectric body 108, 5a housed in a holding casing 13.

FIG. 1 shows a first embodiment of the device of the invention in which drive 102 housed in the casing 13 comprises at least a spring striker 19 causing an electric discharge from a piezoelectric body 5a in the shape of a ceramic cylinder. The piezoelectric body presents opposite end faces covered with two steel discs 7a, 7b. The spring striker 19 is partially housed in a hollow push button 20 retained at a first end 16b of the holding casing 13. The cap 20 comprises an opening having two inclined walls 22 and 23 converging in proximity of a pin 24 passing through the spring striker 19. The push button 20 projects at least partly from a first end 16b of the casing 13 and axially slides in a sliding seat 109a of the holding casing 13. In addition, a spring 26 is placed between the button 20 and the spring striker 19. The spring 26 can be in a compressed condition when the push-button is pressed and thus pushes the striker. Immediately after beginning of a compression, the pin 24 abuts against a shoulder 27 integral with casing 13. Subsequently, as compression goes on, the pin 24 slides along the inclined wall 23 reaching and going beyond the upper end of shoulder 27. At this point the striker 19 is pushed with force against the steel disc 7b and produces delivery of an electric discharge. FIG. 1 also shows a first conductor 10 with its terminal active portion 113a positioned within a second end 16a of the casing. The second end 16a is axially opposed to the first end 16b of the casing. The terminal active portion 113a is axially opposed to the push button (109).

When the push-button 20 is pressed and the striker 19 is pushed against the piezoelectric body 5a, this causes the terminal active portion 113a to move towards the affected skin together with the holding casing. A second conductor is defined by a strap 28 laid down on and partly defining an outer wall of casing 13 and connected to the ceramic cylinder to work as a ground strap when in contact with the body of a user.

For sake of simplicity, FIG. 1 does not show a return spring, the task of which is to bring the spring striker 19 back to the starting position.

FIGS. 2 to 6 show other preferred solutions in accordance with the invention in which the casing 13 is defined by two mutually engaged shells 105 and 106 identical with each other so that a single mold is required for their manufacture. As shown in said figures, the drive is defined by a spring striker 107 (of the same type as described with reference to the embodiment shown in FIG. 1, for example) acting on the voltage-generator 101 which is a piezoelectric body 108 placed inside the casing.

The mutually-engaged shells define a sliding seat 109a for the spring striker 107 which is provided with a driving push-button 109 projecting at least partly from the first end 103 of the holding casing.

Figure 6:
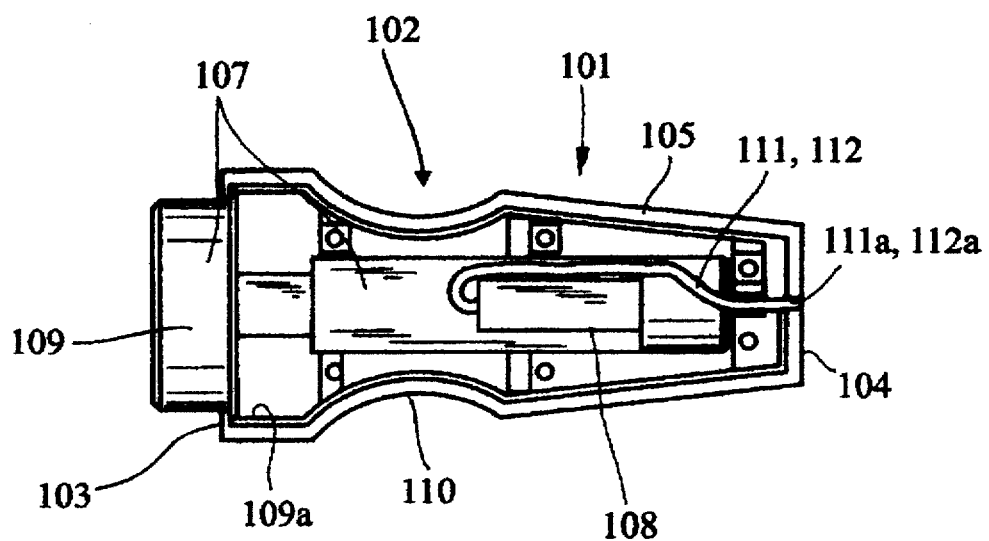
FIG. 6 is a view showing one of the two shells forming the device disclosed in FIG. 3.
Figure 2:
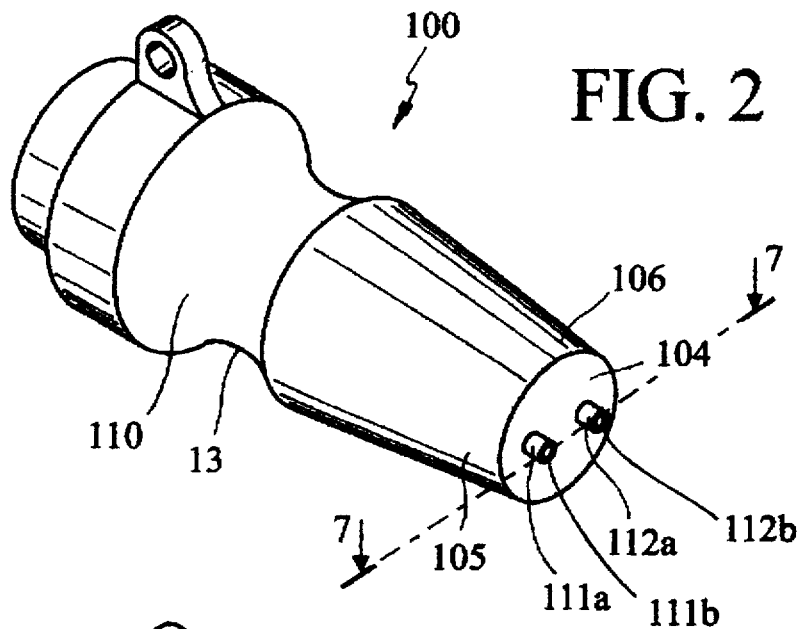
FIG. 2 to 4 are perspective views of other embodiments of the device according to the invention.
Figure 3:
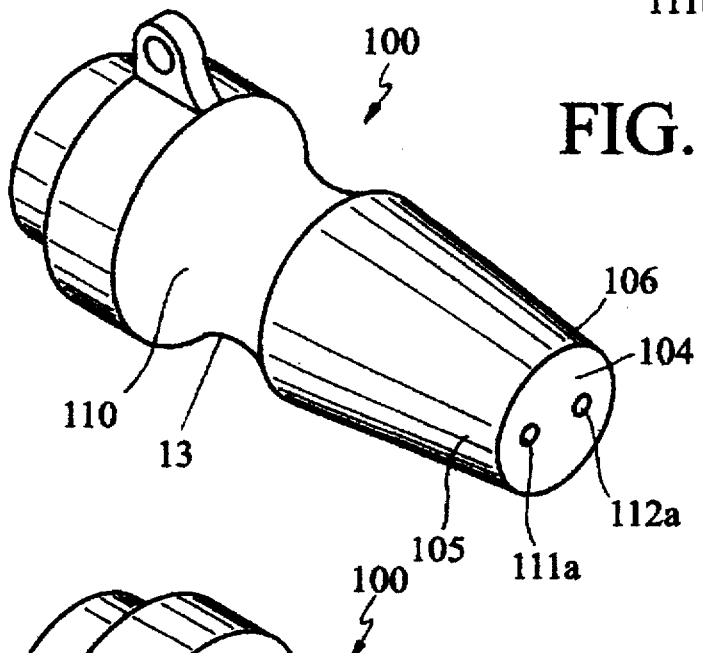

Advantageously, the conformation of each shell also defines an annular engagement seat 110 disposed at a longitudinally intermediate area of the shells to enable the device to be easily handled like a syringe. In the embodiments of FIGS. 2, 3 and 6, the first and second conductor means can be both defined by conductive wires 111, 112 having terminal active portions 111a, 112a which partly project from, or are disposed substantially flush with the second end 104 of said casing (see in this connection FIGS. 2 and 3). In other words the terminal active portions 111a, 112a are axially opposed to the push button 109. In this case, terminal elements 111b, 112b of substantially cylindrical conformation (see FIG. 2) can be preferably associated with the conductive wire terminal active portions.

Figure 5:
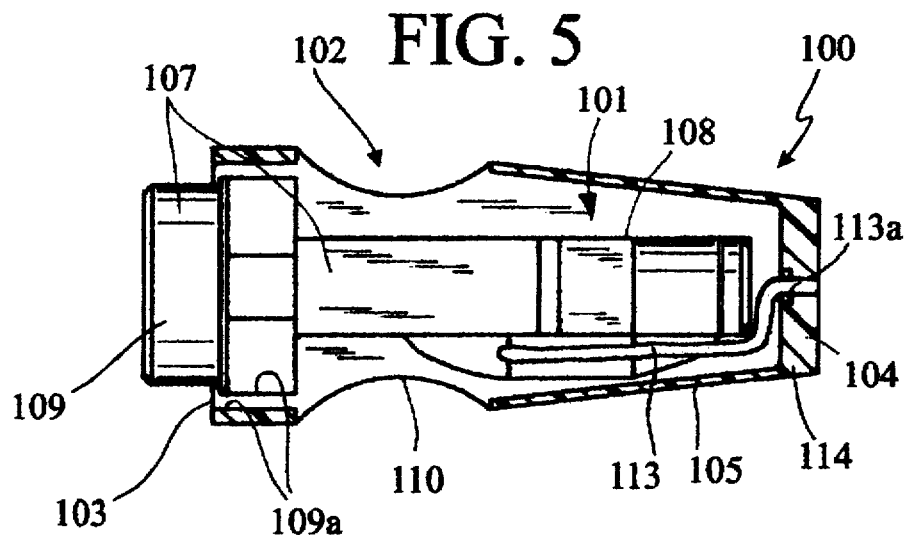
FIG. 5 is a view showing one of the shells of the device disclosed in FIG. 4.
Figure 4:
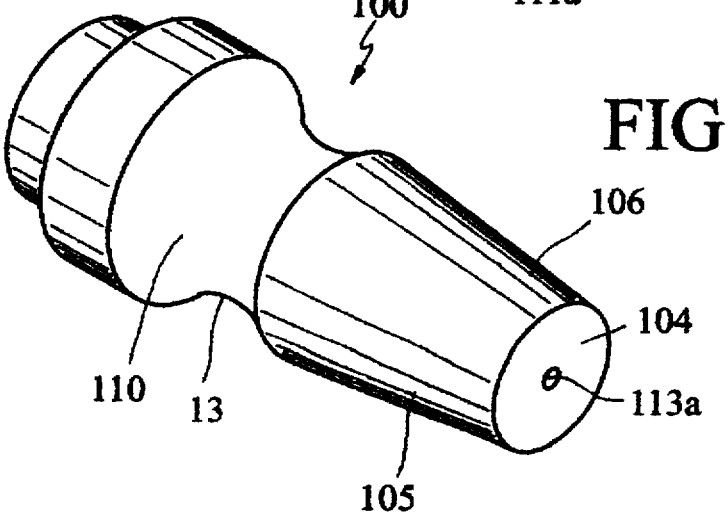

As shown in FIGS. 4 and 5, it is provided that the first conductor means alone is defined by a wire-like conductor 113 having a terminal active portion 113a disposed flush with (see FIG. 4) or partially projecting from, or located backwards relative to the end of the holding casing (not shown). Also in this embodiment the terminal active portion 113a is axially opposed to the push button 109. In this case the second conductor means is defined by the push-button 109 which is made of an electrically conductive material and electrically connected to the piezoelectric body 108.

Therefore in use the circuit is defined by the first conductor, the piezoelectric body, the spring striker, the push-button, the user's body (thumb, hand, arm, trunk, area hit by a bite) and closes on the terminal active portion 113a of the first conductor.

Therefore the electric discharge in this case is directed transversely with respect to the area under treatment and it efficiently passes through the poison or other serum injected by the insect.

Preferably, the second conductor means comprises also the holding casing 13 at least partly made of electrically conductive material electrically connected with the striker or directly with the piezoelectric body. In this case, in order to avoid an electric discharge directly between the terminal active portion 113a of the first conductor and the holding casing, a coating portion 114 of insulating material is advantageously associated with said holding casing 13 and is disposed at the second end 104.

Figure 7:
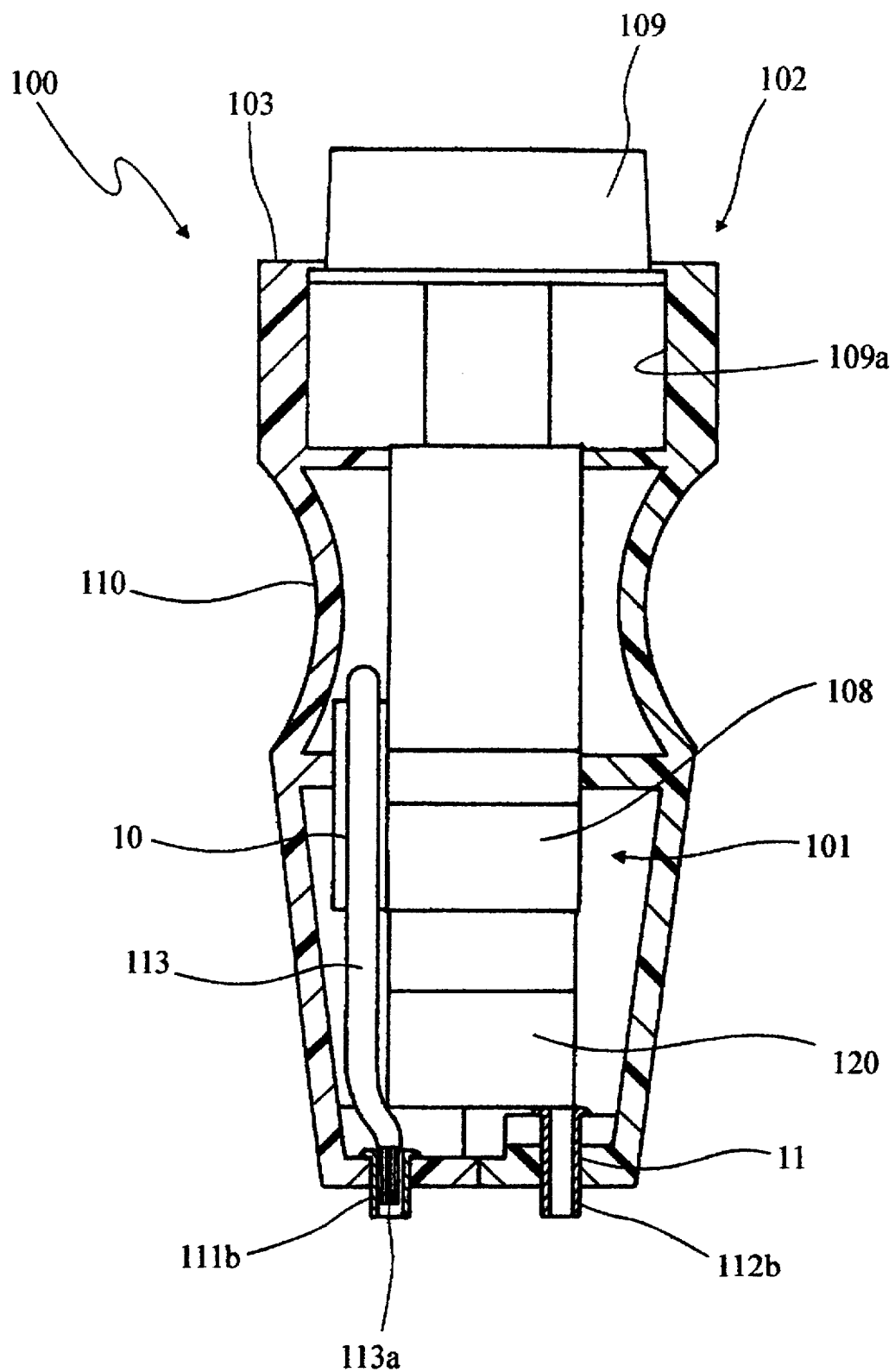
FIG. 7 is a cross-sectional view taken along line VII—VII of FIG. 2.

Finally, as shown in FIG. 7, the first conductor may be defined by an electric conductive wire 113 connected with an end face of the piezoelectric body and having a terminal active portion 113a provided with a terminal element 111b and again axially opposed to the push button. The second conductor is defined by a terminal element 112b having an axial extension greater than the terminal element 111b and directly connected to the other end face of the piezoelectric body. Also the terminal element 112b is axially opposed to the push button 109.

The invention achieves important advantages.

First, a device for treating insect bites of simple and inexpensive structure has been made available.

Second, the use of the piezoelectric body gives the device according to the invention a substantially infinite operative-life.

The present device is capable of generating electric discharges of few kV and more precisely until a maximum value of about 13 kV.

Due to its simple structure the device in question, being very light-in-weight, can be easily carried by a user. At the same time the device is very practical in use, being in the form of a striker.

In addition, the configurations having the first conductor defined by a conductive wire directly active on the user's skin, whereas the second conductor is defined by the casing, by the striker or by the push-button are particularly advantageous. Indeed in these embodiments the first conductor is ground-closed on the user's body thereby causing a discharge transverse to the area to be treated.

These embodiments are particularly advantageous because the electric discharge passes transversely substantially through the whole area hit by a bite.

The invention is also advantageous in its most specific aspects.

Actually, by the use of a conductive-material casing, in the handgrip area the charge intensity per unit surface passing through the user's portion directly in contact with the device is greatly reduced. In addition the use of the coating portion of insulating material is very advantageous; indeed, it makes it substantially impossible for an electric discharge to occur between the casing and the terminal active portion of the first conductive wire when the device is used. Also, when the device is operated far from the patient skin, closure of the circuit on the casing may be obtained with no damage to the piezoelectric body.

What is claimed is:

1. A portable device for treating insect bites comprising:
    a holding casing (13);
    voltage-generating means (101) defined by at least one piezoelectric body (108) having opposite end faces;
    drive means (102) having at least a spring striker (107) housed in said casing and acting at least on an end face of the at least one piezoelectric body (108);
    said drive means (102) having a driving push button (109) operatively connected to the spring striker (107) and axially sliding in a sliding seat (109a) of the holding casing (13), said driving push button (109) projecting at least partly from a first end (103) of the casing (13);
    first and second conductor means each of which is electrically connected with a corresponding end face of the piezoelectric body (108), said first and second conductor means presenting respective terminal active portions (111a, 112a) operating at and with a second end (104) of the casing (13) axially opposed to the first end (103) of the casing (13), said terminal active portions (111a, 112a) being axially opposed to the push button (109).

2. A portable device as claimed in claim 1, wherein the holding casing comprises two shells (105,106) mutually engaged and identical with each other.

3. A portable device as claimed in claim 1, wherein the first and the second conductor means are conductive wires (111, 112) and wherein the active portions (111a, 112a) of the first and of the second conductor means are disposed substantially flush with the second end (104) of said holding casing (13).

4. A portable device as claimed in claim 1 wherein the first and the second conductor means are conductive wires (111, 112) and wherein the active portions (111a, 112a) of the first and the second conductor means partly projects from the second end (104) of said holding casing (13).

5. A portable device for treating insect bites comprising:
a holding casing (13);
voltage-generating means (101) defined by at least one piezoelectric body (108) having opposite end faces;
drive means (102) having at least a spring striker (107) housed in said holding casing (13) and acting at least on an end face of the piezoelectric body (108);
said drive means (102) having also a driving push button (109) operatively connected to the spring striker (107) and axially sliding in a sliding seat (109a) of the holding casing (13), said driving push button (109) projecting at least partly from a first end (103) of the casing (13);
first and second conductor means each of which is electrically connected with a corresponding end face of the piezoelectric body (108),
said first conductor means presenting a terminal active portion (113a) operating at and in correspondence with a second end (104) of the casing (13) axially opposed to the first end (103), said terminal active portion (113a) being axially opposed to said push button (109);
said second conductor means comprising at least the push button (109) made of electrically conductive material.

6. A portable device as claimed in claim 5, wherein the holding casing (13) comprises two shells (105, 106) mutually engaged and identical with each other.

7. A portable device as claimed in claim 5, wherein the second conductor means comprises the holding casing (13) made of electrically conductive material.

8. A portable device as claimed in claim 5, wherein said first conductor means is a conductive wire (113).

9. A portable device for treating insect bites comprising:
a holding casing (13);
voltage-generating means (101) defined by at least one piezoelectric body (108, 5a) having opposite end faces;
drive means (102) having at least a spring striker (107) housed in said holding casing (13) and acting at least on an end face of the piezoelectric body (108,5a);
said drive means (102) having a driving push button (109, 20) operatively connected to the spring striker (107) and axially sliding in a sliding seat (109a) of the holding casing (13), said driving push button (109,20) projecting at least partly from a first end (103, 16b) of the casing;
first and second conductor means each of which is electrically connected with a corresponding end face of the piezoelectric body (108, 5a),
said first conductor means having a terminal active portion (113a) operating at and in correspondence with a second end (104,16b) of the holding casing (13) axially opposed to the first end (103, 16a) of the casing, said terminal active portion (113a) being axially opposed to said push button (109;20);
said second conductor means comprising at least the holding casing (13) at least partly made of electrically conductive material.

10. A portable device as claimed in claim 9, wherein the holding casing (13) comprises two shells (105, 106) mutually engaged and identical with each other.

11. A portable device as claimed in claim 9, wherein said first conductor means is defined by a conductive wire (113).

12. A portable device as claimed in claim 9, comprising a coating portion (114) of insulating material operatively associated with said second end (104) of the casing (13).

* * * * *